US005567599A

United States Patent [19]
Lemieux

[11] Patent Number: 5,567,599
[45] Date of Patent: Oct. 22, 1996

[54] METHOD FOR PRODUCING TRANSFORMED CHRYSANTHEMUM PLANTS

[75] Inventor: Christine S. Lemieux, Oakland, Calif.

[73] Assignee: Florigene Europe B.V., Rijnsburg, Netherlands

[21] Appl. No.: 251,392

[22] Filed: Jan. 26, 1994

Related U.S. Application Data

[63] Continuation of Ser. No. 570,575, Aug. 21, 1990, abandoned.

[51] Int. Cl.⁶ .......................... C12N 15/00; C12N 15/82
[52] U.S. Cl. ................... 435/172.3; 435/172.1; 435/240.4; 435/240.49; Plt./74.1; 800/205
[58] Field of Search .................... 435/172.3, 172.1, 435/240.4, 240.45, 240.46, 240.49; Plt./74.1

[56] References Cited

U.S. PATENT DOCUMENTS

| | | | |
|---|---|---|---|
| 4,616,099 | 10/1986 | Sparkes | Plt./74 |
| 4,827,061 | 5/1989 | VandenBerg | Plt./74 |
| 5,034,323 | 7/1991 | Jorgensen et al. | 435/172.3 |

FOREIGN PATENT DOCUMENTS

| | | | |
|---|---|---|---|
| 0193259 | 9/1986 | European Pat. Off. | C12N 15/00 |
| 0275069 | 7/1988 | European Pat. Off. | 435/172.3 |
| 8501856 | 9/1985 | WIPO | 435/172.3 |

OTHER PUBLICATIONS

Stachel et al. (1985) Nature vol. 318 pp. 624–629.
Potrykus (1990) Biotechnology pp. 535–542.
Horsch et al., 1986, Proc. Nat. Acad. Sci. 83:2571–2575.
Horsch et al., 1985, Science 227:1229–1231.
Peerbolte et al., 1987, Plant Molecular Biology 9:51–57.
Earle et al., 1974, J. Amer. Soc. Hort. Sci. 99(4):352–358.
Earle et al., 1974, J. Amer. Soc. Hort. Sci. 99(2):28–31.
Kaul et al., 1990, Plant Cell, Tissue and Organ Culture 21:21–30.
Broertjes et al., 1976, Euphytica 25:11–19.
Hill, 1968, Physiol. Plant. 21:386–389.
Earle et al., 1974, J. Amer. Soc. Hort. Sci. 99:128–132.
Bush et al., 1976, Amer. J. Bot. 63:729–737.
Swangan et al., 1977, Acta Hortic., 78:237–242.
Khalid et al., 1989, Scientia Horticulturae 38:287–294.
Sutter et al., 1981, Ann. Bot. 48:559–568.
Roest et al., 1975, Scientia Horticulturae 3:317–330.
Lu et al., 1990, Plant Cell Reports 8:733–736.
Sauvadet et al., 1990, Plant cell reports 8:692–695.
Lorz et al., 1985, Mol. Genet. 199:178–182.
Hess, 1978, Z. Planzinphysiol. 90:119–132.
Ohta, 1986, Proc. Natl. Acad. Sci. U.S.A. 83:715–719.
Chilton et al., 1977, Cell 11:263–271.
Fraley et al., 1986, CRC Critical Reviews in Plant Science 4:1–46.
Hoogkeas–Van Slogteren et al., 1984, Nature 311:763–764.
Potrykus et al., 1985, Nature 311:183–188.
McHughen et al., 1989, J. Plant Physiol. 135:245–248.
Konwar et al., Progress in Plant Cellular and Molecular Biology, HJJ Nijkamp; LHW van der Plas, J van Aartijk, eds., Kluer Acad. Publ. 1990, pp. 114–118 (Konwor).
Schneider et al., 1987, Biochem. Physiol. 182:485–490.
van Geyt et al., 1985, Plant Cell Reports 4:66–69.
Saunders et al., 1984, Plant Science Letters 34:219–223.
van Wordragen et al., 1989, J. Cell Biochem. Supp. 13D, p. 271.
van Wordragen et al., 1990, Abstracts VIIth International Congress on Plant Tissue and Cell Culture, Amsterdam, Jun. 24–29.
Hutchinson et al., 1989, J. Cell Biochem. Supp. 13D, p. 261.
Stewart et al., 1970, Am. J. Bot. 57:734–735.
Poster–U. C. Davis Aug. 21, 1989.
Abstract (Lemieux). Published on or after Aug. 21, 1990.
DNAP Abstract—VIIth Int'l Congress on Plant Tissue and Cell Culture Jun. 24, 1990.

*Primary Examiner*—Gary Benzion
*Attorney, Agent, or Firm*—Townsend and Townsend and Crew LLP

[57] ABSTRACT

The invention is directed to a method for introducing an exogenous DNA fragment(s) into a chrysanthemum plant using Agrobacterium as a vector. The invention is further directed to the transformed chrysanthemum plant produced therefrom.

61 Claims, 3 Drawing Sheets

METHOD FOR PRODUCING TRANSFORMED CHRYSANTHEMUM PLANTS

This is a Continuation of application Ser. No. 07/570,575, filed Aug. 21, 1990, now abandoned.

1. FIELD OF THE INVENTION

The invention is directed to a method for producing a chrysanthemum plant which comprises and is capable of expressing an exogenous DNA fragment using Agrobacterium as a vector. The invention is further directed to the transformed chrysanthemum plant produced according to such a method.

2. BACKGROUND OF THE INVENTION

2.1. IN VITRO REGENERATION OF CHRYSANTHEMUM

The chrysanthemum, Chrysanthemum x hortorum (Bailey) L. H., Compositae, alternatively known as *Chrysanthemum moripholium* (Ramat) or *Dendranthema grandiflora* (Tzvelev is one of the most important cut flower crops (Kaul et al., 1990, Plant Cell, Tissue and Organ Culture 21:21–30). New cultivars of chrysanthemum have primarily been generated by crossbreeding (see for example VandenBerg, U.S. Pat. No. 4,827,061, issued May 2, 1989) or by mutation breeding (see for example Sparkes, U.S. Pat. No. 4,616,099, issued Oct. 7, 1986 and Broertjes et al., 1976, Euphytica 25:11–19). However, such procedures are tedious and may be unpredictable. Additionally, it may be difficult to determine the genotype of a cultivar generated by these methods.

It would be desirable to use recombinant DNA technology to confer characteristics such as new color, increased flower life, and disease and insect resistance to plants reproducibly and efficiently. However, in order to use such recombinant DNA technology, it is necessary that there be methods for transferring exogenous DNA fragments into a chrysanthemum plant. As will be described in further detail in Section 2.2. infra, attempts to transform chrysanthemum plants with exogenous DNA fragments using Agrobacterium as a vector have had only limited success. There must also be methods for efficiently culturing chrysanthemum plants in vitro. As will be discussed below, in vitro shoot multiplication, adventitious regeneration in chrysanthemum, and regeneration from cultured protoplasts have been reported by several groups.

Chrysanthemum regeneration was initially achieved using a callus intermediary (Hill, 1968, Physiol. Plant. 21:386–389). Explants of a chrysanthemum stem and receptacle were cultured on medium containing 2 mg/l naphthalene acetic acid (NAA) and 0.8 g/l kinetin and then subcultured on medium containing 1 mg/l kinetin, resulting in the production of callus and the ultimate production of shoot formation. Earle and Langhans (1974, J. Amer. Soc. Hort. Sci. 99:128–132) obtained single or multiple shoots and leafy basal callus in shoot tip culture using medium containing 2 mg/l kinetin and 0.02 mg/l NAA. Bush et al. (1976, Amer. J. Bot. 63:729–737) obtained plant regeneration from petal derived callus using medium containing 1 mg/l 6-benzyladenine (6-BA) and 1 mg/l indole acetic acid (IAA). Sangwan and Harada (1977, Acta Hortic. 78:237–242) placed various explants on media containing 2,4-dichlorophenoxy acetic acid (2,4-D) . The calli produced were used to initiate suspension cultures which they then regenerated.

Culturing of a chrysanthemum plant using a callus intermediary, however, may result in unexpected variations. For example, regeneration through a callus phase has resulted in changes in flower color and/or shape in some chrysanthemum cultivars (Khalid et al., 1989, Scientia Horticulturae 38:287–294 and Bush et al., 1976, Amer. J. Bot. 63:729–737). Abnormalities such as aberrant forms, proliferation of apical buds, variable leaf shapes and stunted growth have also been observed in plants regenerated from long term callus cultures (Sutter and Langhans, 1981, Ann. Bot. 48:559–568).

Methods have also been developed for directly producing shoots from explant tissue. Such procedures may help retain clonal fidelity. Roest and Bokelmann (1975, Scientia Horticulturae 3:317–330) reported the development of shoots using pedicels from chrysanthemum cultivars (Super Yellow, Bravo). The Super Yellow was cultivated in medium containing 1 mg/l 6-BA and 0.01 mg/l IAA. The Bravo cultivar was incubated in medium containing 1 mg/l 6-BA and 1 mg/l IAA. Recently, shoot regeneration from stem and leaf explants have been observed (Kaul et al., 1990, Plant Cell, Tissue and Organ Culture 21:21–30 and Lu et al., 1990, Plant Cell Reports 8:733–736). Both sets of investigators found that optimum results were achieved using 6-BA and NAA.

A third approach involves the use of chrysanthemum mesophyll protoplasts (Sauvadet et al., 1990, Plant Cell Reports 8:692–695). The best results were observed using medium that did not contain ammonium sulfate. Twenty-nine clones were studied. Calli were observed in five of the clones. Complete regeneration was observed in one of the clones.

2.2. TRANSFER OF EXOGENOUS DNA INTO A FLOWERING PLANT

With the advent of genetic engineering, it has become a major goal to modify and improve plants by introducing foreign genes encoding important functional traits. Such traits include resistance to herbicides, pesticides or pests; tolerance to cold, heat, drought, or salinity; and changes in flower color. A number of approaches currently exist for transferring heterologous or exogenous gene(s) or gene sequences(s) into the genome of plants, also known as plant transformation.

One approach, known as direct transformation, induces uptake and integration of plasmid or linearized DNA in the genome of plant protoplasts, i.e. single cells stripped of cell wall material (Lorz et al., 1985, Mol. Genet. 199:178–182). When protoplasts and DNA molecules are incubated together, under proper inducing conditions (i.e. the use of polyethylene glycol, liposomes and/or electroporation), DNA is taken up and integrated into the plant genome. The frequency of transformation is highly variable, however, and few major crop plants can be regenerated from protoplasts.

A second approach involves the transfer of exogenous bacteriophage or plasmid DNA into germinating pollen grains to modify plant properties. As the pollen tube emerges from the mature pollen grain, cell wall material is deposited behind the growing tip. Therefore, immediately behind the growing point, the cell wall is just beginning to form. Exogenous DNA may be able to enter the male gametophyte, and be carried to the egg during the course of pollen tube growth and fertilization (see for example Hess, 1978, Z.

Planzinphysiol. 90:119–132; DeWet, PCT Patent Application WO 85/01856, 1985; Ohta, 1986, Proc. Natl. Acad. Sci. U.S.A. 83:715–719; EPO Application No. 275,069, published Jul. 20, 1988; U.S. application Ser. No. 347,831, filed May 5, 1989).

A third approach relies on infection by Agrobacterium bacterium, which inserts sequences of a plasmid, known as the Ti-plasmid, into the genome of plant cells (Chilton et al., 1977, Cell 11:263–271). Agrobacterium-mediated plant transformation has been demonstrated in many dicots (see Fraley et al., 1986, CRC Critical Reviews in Plant Science 4:1–46) as well in monocots, e.g., Chlorophytum and Narcissus (Van Slogteren et al., 1984, Nature 311:763–764), Lolium (Potrykus et al., 1985, Mol. Gen. Genet. 199:183–188). It has recently been shown that preculture of explants in medium containing 6-BA and NAA prior to Agrobacterium inoculation increases production of transgenic flax (McHughen et al., 1989, J. Plant Physiol. 135:245–248). Preculture of shoots in media containing plant hormones has also been used in the regeneration of nontransformed sugarbeets (Konwar and Couts, in Progress in Plant Cellular and Molecular Biology, H. J. J. Nijkamp; L. H. W. van der Plas, J. van Aartrijk, eds., Kluwer Acad. Publ. 1990, pp. 114–118; Schneider and Gunther, 1987, Biochem. Physiol. 182:485–490; van Geyt and Jacobs, 1985, Plant Cell Reports 4:66–69; Saunders and Daub, 1984, Plant Science Letters 34:219–223).

Agrobacterium-mediated transformation of exogenous DNA has been attempted in chrysanthemum plants. Van Wordragen et al., (1989, J. Cell Biochem. Supp. 13D, 271) attempted to develop an Agrobacterium-mediated transformation for *Chrysanthemum morifolium* by infecting leaf disks of sterile plantlets with two virulent Agrobacterium strains: *A. tumefaciens* A281 (pTVK291) and *A. rhizogenes* LBA9402. A281 induces agropine/mannopine-producing tumors and LBA9402 induces agropine/mannopine-producing hairy roots on a large number of plants. In this instance, tumors on the leaf disks, but not hairy roots, were observed. Additionally, no shoot formation was observed; therefore, regeneration was not achieved. Additionally, van Wordragen et al., (1990, Abstracts VIIth International Congress on Plant Tissue and Cell Culture, Amsterdam, Jun. 24–29, 1990) reported that no transformed shoots were observed when *Chrysanthemum morifolium* was incubated with *A. tumefaciens* LBA4404 (pBI112). Hutchinson et al. (1989, J. Cell Biochem. Supp. 13D, 261) reports adventitious shoot regeneration from stem and leaf explants in *Chrysanthemum morifolium* inoculated with Agrobacterium containing an exogenous DNA fragment but does not provide any evidence that transformation indeed occurred.

3. SUMMARY OF THE INVENTION

The invention is directed to a method for producing a chrysanthemum plant comprising an exogenous DNA fragment(s), in which the chrysanthemum plant is capable of expressing the exogenous DNA fragment(s), comprising the steps of:

(a) isolating an explant from source material from a chrysanthemum plant;

(b) inoculating the explant from source material from the chrysanthemum plant with a culture of Agrobacterium, which Agrobacterium comprises an exogenous DNA fragment(s) comprising a gene(s) under the control of a promoter capable of promoting the transcription of the gene within the exogenous fragment, to obtain an inoculated explant;

(c) incubating the inoculated explant of step (b) on an incubation medium;

(d) culturing the incubated explant of step (c) on a regeneration medium to obtain regenerated shoots of the chrysanthemum plant and;

(e) culturing the regenerated shoots of step (d) on a rooting medium to obtain a chrysanthemum plant comprising the exogenous DNA fragment(s), in which the chrysanthemum plant is capable of expressing the gene(s) within the exogenous DNA fragment(s).

In a preferred embodiment, the source material is sterilized. The method may in a specific embodiment further comprise the step incubating the explant source material on a pretreatment medium before isolating the explant.

The method may also further comprise detecting the presence of the exogenous DNA fragment in the chrysanthemum plant to confirm the transformation event using procedures known in the art (See Section 5.7., infra).

The invention further relates to chrysanthemum plants comprising an exogenous DNA fragment(s) and are capable of expressing the gene(s) within the exogenous DNA fragment(s), which may be obtained using the method of the present invention. The traits encoded by such such a DNA fragment(s) include but are not limited to a new flower color, herbicide or pesticide resistance, disease resistance and/or resistance to adverse environmental conditions such as temperature extremes. The chrysanthemum plant may further comprise an exogenous DNA fragment encoding a selectable marker.

The invention also relates to a method for obtaining a somaclonal variant of a chrysanthemum plant comprising:

(a) isolating an explant from source material from a chrysanthemum plant;

(b) inoculating the explant from source material from a chrysanthemum plant with a culture of Agrobacterium to obtain an inoculated explant;

(c) incubating the inoculated explant of step (b) on a solid incubation medium;

(d) culturing the incubated explant of step (c) on a regeneration medium to obtain regenerated shoots of the chrysanthemum plant; and (e) culturing the regenerated shoots of step (d) on a rooting medium to obtain a mature plant; and (f) recovering the somaclonal variant.

3.1. DEFINITIONS

As used herein, "chrysanthemum plant" refers to any plant that is a member of the genus Chrysanthemum. This includes a wide variety of public and private (e.g., Fides, Yoder Brothers) lines, e.g., Puritan, Lipstick, Indianapolis White Giant, Indianapolis Dark Bronze, Moneymaker, Mundial, Tiger, Impala, Hebo, Toon Hermans, Marina, Happy. Also included are potted chrysanthemums (e.g., Gem series, Applause, Charm series, Spark); standard chrysanthemums (e.g., Bounty, Hartmanns series, Copper Anne); garden chrysanthemums (e.g., Prophets Series, Mascot series); and spray chrysanthemums (e.g., Superstar, Nova series, Marble series).

"Exogenous DNA fragment" as used herein refers to any DNA fragment that is not resident in the genome of the plant being transformed.

"Nutrient media" as used herein refers to media that comprises salts, a carbon source and vitamins at concentrations necessary to effect the maintenance of cultured plant cells.

"Effective amounts" as used herein refers to the amount of a given component necessary to effect the recited step.

5. DETAILED DESCRIPTION OF THE INVENTION

The invention is directed to methods for transferring an exogenous DNA fragment (s) into an explant of a chrysanthemum plant and obtaining at least one regenerated chrysanthemum plant comprising the exogenous DNA fragment(s) and which is capable of expressing the exogenous DNA fragment(s). Five steps are involved in obtaining a regenerated chrysanthemum plant containing the exogenous DNA fragment(s): (a) isolating an explant from source material from a chrysanthemum plant; (b) inoculating the explant from source material from the chrysanthemum plant with a culture of Agrobacterium, which Agrobacterium comprises an exogenous DNA fragment(s) comprising a gene(s) under the control of a promoter capable of promoting the transcription of the gene(s) within the exogenous fragment(s), to obtain an inoculated explant; (c) incubating the inoculated explant of step (b) on an incubation medium; (d) culturing the incubated explant of step (c) on a regeneration medium to obtain regenerated shoots of the chrysanthemum plant; and (e) culturing the shoots of step (c) on a rooting medium to obtain a chrysanthemum plant comprising the exogenous DNA fragment(s) in which the chrysanthemum plant is capable of expressing the gene(s) within the exogenous DNA fragment(s). The presence of the exogenous DNA fragment(s) may be detected using procedures known in the art (see Section 5.7., infra).

5.1. ISOLATION AND STERILIZATION OF CHRYSANTHEMUM PLANT EXPLANTS

Explants may for example be obtained from such source materials as the leaf, stem, or petiole; from the peduncle or other reproductive parts; or from the shoot tip itself which includes the meristem and leaf primordia. These source materials as described in Section 5.2., infra, can be pretreated. Leaf, petiole, and shoot tip explants may be obtained by growing the chrysanthemums at long day greenhouse conditions e.g., 8–9 hours dark or by in vitro culture using techniques known in the art (see Section 2.2., supra for examples). The leaf and petiole may be subsequently cut into sections. Shoot tips (apex+2–4 leaf primordia) 0.2–1 cm in length are dissected from the shoot and either cut in half or left as is. Peduncle explants may be obtained by growing the chrysanthemum plant under long day greenhouse conditions, and then for 1–6 weeks under short day conditions. Peduncles may be cut into sections up to 10 cm from the apex either transversely or longitudinally.

Nodal cuttings (containing a node) or apical cuttings (top of the plant) may be sterilized with bleach, e.g. chlorine bleach. In a specific embodiment, 10–30% clorox/0.1% detergent solution (e.g., Tween 80) is used, followed by a water rinse.

5.2. PRETREATMENT OF THE EXPLANT SOURCE

In a preferred embodiment, the shoot culture, which is one source of the explant, is obtained from the chrysanthemum shoot tip. Non-sterile plant material may be removed from the shoot tip in such a way as to preserve the sterility of the apical dome. Alternatively, apical cuttings may be sterilized as in Section 5.1., supra. The shoot tip is placed in a pretreatment media which comprises effective amounts of a nutrient medium, an energy source, iron, and a cytokinin. The nutrient media may be selected from the group including but not limited to MS, LS, White's, N6, and B5 medium. The energy source may in a specific embodiment may be a sugar (e.g. sucrose) at a concentration of 0.5–5% (w/v). The iron may be present at a concentration of about 25–200 mM. The cytokinin may include but is not limited to 6-benzyladenine (6-BA), zeatin (ZEA), kinetin (KIN), isopentyladenosine (2-iP), and thidiazuron, or riboside derivatives of any of the foregoing. If the cytokinin is 6-benzyladenine (6-BA), zeatin (ZEA), kinetin (KIN), isopentyladenosine (2-iP), the cytokinin is present in a preferred embodiment at a concentration of about 0.1–10 mg/l (w/v). If the cytokinin is thidiazuron, the cytokinin is present at a concentration of about $10^{-4}$–$10^{-2}$ mg/l. The pretreatment media in a specific embodiment may comprise 0.5–5.0 mg/l 6-BA and 1–10 mg/l kinetin. The pretreatment media may further comprise an auxin at a concentration up to about 0.5 mg/l. The auxin may be any auxin, natural or synthetic, for example, indole acetic acid (IAA), naphthalene acetic acid (NAA), (2,4-dichlorophenoxy) acetic acid (2,4-D) and picloram. In preferred embodiments, the pretreatment media comprises in addition to nutrient medium, about 1 mg/l 6-BA and about 0.02 mg/l NAA or alternatively about 2 mg/l kinetin and about 0.02 mg/l NAA. Prior to inoculation, the explant source is incubated on the pretreatment for about 1 day to about 7 months, preferably about 1 day to about 3 months. The shoot is maintained indefinitely on pretreatment medium.

5.3. INOCULATION OF CHRYSANTHEMUM PLANT EXPLANTS WITH AROBACTERIUM COMPRISING EXOGENOUS DNA

Inoculation of chrysanthemum plant explants with an exogenous DNA fragment is carried out with Agrobacterium comprising an exogenous DNA fragment. In general, it is known that a preferred method of introducing an exogenous DNA fragment into plant cells is to infect a plant or explant of the plant with *Agrobacterium tumefaciens* containing the fragment. The exogenous DNA fragment may as will be described in further detail in Section 5.8., infra, encode traits such as new colors or color patterns, herbicide resistance, disease resistance, or resistance to environmental extremes.

The Agrobacterium may further comprise an exogenous DNA fragment encoding a selectable marker or functionally active portion thereof (e.g. kanamycin resistance, spectinomycin resistance, hygromycin resistance). If a transformed chrysanthemum plant comprises such a marker gene, it will grow in medium containing a selection agent (see Section 5.5, infra). The Agrobacterium may alternatively further comprise an exogenous DNA fragment encoding a reporter substance such as β-glucuronidase or luciferase. The presence of the reporter may be detected as described in Section 5.5, infra.

The exogenous DNA fragment(s) may be introduced into appropriate plant cells, for example, by means of the Ti plasmid of *Agrobacterium tumefaciens*. The Ti plasmid is transmitted to plant cells upon infection by *Agrobacterium tumefaciens*, and is stably integrated into the plant genome (Ho, 1984, Science 233:496–498; Fraley et al., 1983, Proc. Natl. Acad. Sci. U.S.A. 80:4803).

The Ti plasmid contains two regions essential for the production of transformed cells. One of these, named transfer DNA (T DNA), induces tumor formation. The other, termed virulent region, is essential for the introduction of T DNA into plant cells. The transfer DNA region, which transfers to the plant genome, can be increased in size by the insertion of the exogenous DNA fragment without its transferring ability being affected. By removing the tumor-causing genes so that they can no longer interfere, the modified Ti plasmid can then be used as a vector for the transfer of the gene constructs of the invention into an appropriate plant cell, such being a "disarmed" (i.e.,disabled) Ti vector (Zambryski et al., 1983, EMBO J. 2:2143–2150).

One way to employ the Agrobacterium system is to use a the binary system, wherein to have infection, two plasmids are used: a T-DNA containing plasmid and a vir plasmid. Any one of a number of T-DNA containing plasmids can be used, the only requirement being that one be able to select independently for each of the two plasmids.

The Agrobacterium in a preferred embodiment comprises a heterologous promoter which promotes the transcription of a gene(s) within the exogenous DNA fragment(s). Examples include but are not limited to the Cauliflower Mosaic Virus 35S promoter, or 1' promoter or 2' promoter or nopaline synthetase (nos) promoter. Any infectlye disarmed Agrobacterium strain (e.g. LBA4404, Hoekema et al., 1983, Nature (London) 303:179–181) containing engineered Ti plasmid with a DNA fragment capable of being transferred to and of functioning in plant cells may be used. Agrobacterium cultures may be maintained and grown on any bacterial medium, e.g., M9, LB, MinA, that will support growth of Agrobacterium. The cultures may be resuspended in liquid culture and grown overnight or used minutes later.

Cocultivation of the Agrobacterium culture with the explant involves procedures known in the art (see for example Rogers et al., Methods For Plant Molecular Biology, eds. A. Weissbach and H. Weissbach, Academic Press, N.Y., 1988, pp. 423–436). In a preferred embodiment, explants are contacted with bacterial solution. The solution is removed by pipetting 1–60 minutes later.

5.4. INCUBATION

The inoculated explants may in one embodiment be incubated on incubation medium to facilitate transformation which comprises effective amounts of a nutrient medium, an energy source, iron, and a cytokinin, for 1–5 days at 16°–28° C. In a preferred embodiment, the inoculated explants are plated on filter paper on solid incubation medium for 2–3 days at 20°–24° C. The nutrient media may be selected from the group including but not limited to MS, White's, N6, LS, and B5 medium. The energy source may in a specific embodiment be a sugar (e.g. sucrose) at a concentration of 0.5–5% (w/v). The cytokinin may include but is not limited to 6-benzyladenine (6-BA), zeatin (ZEA), kinetin (KIN), isopentyladenosine (2-iP), and thidiazuron, or any of the riboside derivatives of any of the foregoing. If the cytokinin is 6-benzyladenine (6-BA), zeatin (ZEA), kinetin (KIN), or isopentyladenosine (2-iP), the cytokinin is present in a preferred embodiment at a concentration of about 0.1–10 mg/l (w/v). If the cytokinin is thidiazuron, the cytokinin is present at a concentration of about $10^{-4}$–$10^{-2}$ mg/l. The incubation medium may further comprise an auxin. The auxin may be any auxin, natural or synthetic, for example, indole acetic acid (IAA), naphthalene acetic acid (NAA), (2,4-dichlorophenoxy) acetic acid (2,4-D) and picloram. In a preferred embodiment, the auxin is present at a concentration up to about 2 mg/l. The incubation medium may further comprise acetosyringone at a concentration up to about 500 µM. In a preferred embodiment, acetosyringone is present at a concentration of about 200 µM.

The optimum concentration of cytokinin and auxin may be determined by culturing the explant before being inoculated with the Agrobacterium in media containing varying concentrations of cytokinin and auxin. The number of explants with shoots are evaluated after culturing for four weeks. Concentrations of cytokinin which range from 0.1–10 mg/l for cytokinins 6-benzyladenine (6-BA), zeatin (ZEA), kinetin (KIN), isopentyladenosine (2-iP) and from $10^{-4}$–$10^{-2}$ mg/l for the cytokinin, thidiazuron and auxin (0–2 mg/l) that will give at least 50% of the explants producing shoots are chosen.

5.5. REGENERATION

After the incubation step, the explant optionally may be washed with an antibiotic solution for a period of several minutes to several hours. Any antibiotic effective against Agrobacterium and nontoxic to plants may be used. Such antibiotics may include but are not limited to carbenicillin, cefotaxime, or vancomycin and may be used in the regeneration step described below.

The incubated explant is then cultured in regeneration medium to obtain regenerated shoots of the chrysanthemum plant. Regeneration medium comprises effective amounts of a nutrient medium, an energy source, a cytokinin, and a counter selection agent. The nutrient media may be selected from the group including but not limited to MS, White's, N6, LS, and B5 medium. The energy source may in a specific embodiment may be a sugar (e.g. sucrose) at a concentration of about 0.5–5% (w/v). The cytokinin may include but is not limited to 6-benzyladenine (6-BA), zeatin (ZEA), kinetin (KIN), isopentyladenosine (2-iP), and thidiazuron, or riboside derivatives of any of the foregoing. If the cytokinin is 6-benzyladenine (6-BA), zeatin (ZEA), kinetin (KIN), isopentyladenosine (2-iP), the cytokinin is present in a preferred embodiment at a concentration of about 0.1–10 mg/l (w/v). If the cytokinin is thidiazuron, the cytokinin is present at a concentration of about $10^{-4}$–$10^{-2}$ mg/l. The regeneration medium may further comprise an auxin. The auxin may be any auxin, natural or synthetic, for example, indole acetic acid (IAA), naphthalene acetic acid (NAA), (2,4-dichlorophenoxy) acetic acid (2,4-D) and picloram. In a preferred embodiment, the auxin is present at a concentration up to about 2 mg/l. The counter selection agent kills Agrobacterium. The counter selection agent may include but is not limited to carbenicillin (250–1000 mg/l), cefotaxime (250–1000 mg/l), or vancomycin (100–500 mg/l).

If the Agrobacterium comprises a DNA fragment encoding a selectable marker, the regeneration medium may further comprise a selection agent. Such a selection medium may be used to select for transformants. If the selectable marker is kanamycin resistance, the selection agent is kanamycin. If the selectable marker is hygromycin resistance, the selection agent is hygromycin. If the selectable marker is spectinomycin resistance, the selection agent is spectinomycin.

If the Agrobacterium comprises a DNA fragment encoding a reporter, e.g. a screenable marker, detection may involve the use of a reporter agent, specifically, a substrate or other agent which identifies the reporter. Regenerated plants may be assayed using an assay buffer or assay medium. If the reporter is β-glucuronidase, the reporting agent is X-glucuronic acid. If the reporter is luciferase, the reporting agent is luciferin.

The optimum level of selection or reporting agent used is dependent on the promoter originally introduced into the Agrobacterium and the variety of chrysanthemum. For example, if a nos promoter is introduced and the selectable marker is kanamycin resistance, the selection medium should contain 25–100 mg/l kanamycin. If a 35S promoter is introduced and the selectable marker is kanamycin resistance, the selection medium should contain 75–250 mg/l kanamycin. If a 35S promoter is introduced and the selectable marker is hygromycin resistance, the selection medium should contain 20–40 mg/l hygromycin. If a 35S promoter is introduced and the selectable marker is spectinomycin resistance, the selection medium should contain 75–250 mg/l spectinomycin. In a preferred embodiment, the selection medium comprises nutrient medium, 2.0 mg/l 6-BA, 1.0 mg/l NAA, 500 mg/l carbenicillin and 100 mg/l kanamycin. Even if the Agrobacterium comprises a DNA fragment encoding a selectable marker, the selection agent can be omitted, with selection taking place in rooting medium as described in Section 5.6., infra.

The incubated explant is cultured on regeneration medium for 10–60 days, preferably 20–40 days at 20°–25° C. In a preferred embodiment, during each day of the culture period, the mixture is cultured for 16 hrs. at 1500–3000 lux under plant spectrum lights and for 8 hrs. in a dark growth room.

5.6. PLANTLET PRODUCTION

Mature shoots obtained from culturing the incubated explant in a regeneration medium are transferred to a rooting medium to obtain mature plant lets. Rooting medium comprises effective amounts of a nutrient medium, an energy source, and a counter selection agent. The nutrient media may be selected from the group including but not limited to MS, White's, N6, and B5 medium. The energy source may in a specific embodiment may be a sugar (e.g. sucrose) at a concentration of about 0.5–5% (w/v). The counter selection agent may include but is not limited to carbenicillin (250–1000 mg/l), cefotaxime (250–1000 mg/l), or vancomycin (100–500 mg/l). The rooting medium, like the regeneration medium may further comprise a selection agent, using selection agents described in Section 5.5. supra.

5.7. CONFIRMATION OF TRANSFORMATION

Transformation may be confirmed using procedures known in the art. For instance, confirmation may be accomplished by putting the shoot in a rooting medium comprising a selection agent, as in Section 5.6., supra. In another embodiment, leaf callus pieces removed from transformed shoots are placed on a callus medium which may comprise effective amounts of a nutrient medium, one or more growth regulator(s), i.e. phytohormones, an energy source, and a selection agent, specific examples of which are described in Section 5.4, supra and subsequently determining the callus response of the leaf pieces to these growth conditions.

The presence of a reporter gene may also be determined to confirm transformation, e.g., by GUS (β-glucuronidase) or luciferase assays, if the Agrobacterium comprises a DNA fragment encoding a β-glucuronidase or luciferase gene, by using procedures known in the art. See for example, Jefferson et al., 1986, Proc. Natl. Acad. Sci. U.S.A. 83:8447–8451 (GUS) and Ow et al., 1986, Science 234:856–859 (luciferase).

The exogenous DNA fragment may be detected by DNA detection means using procedures known in the art. These include but are not limited to Polymerase Chain Reaction (PCR) technology, restriction enzyme digestion, Southern blot hybridization, and Northern blot hybridization (see for example Maniatis et al., 1989, Molecular Cloning, A Laboratory Manual, Cold Spring Harbor Laboratory, Cold Spring Harbor, N.Y.).

5.8. APPLICATIONS AND USES

The method of the invention may be used to introduce a wide variety of gene-encoded traits in the chrysanthemum plants using genes from any source (e.g., bacterial, fungal, plant, mammalian). Examples of such traits included new colors or color patterns (e.g., encoded by genes for indigo, delphinidin, anthocyanin, carotenoids, betalains); herbicide resistance (e.g., chlorosulfuron, glyphosphate, sulfonylurea); pesticide or disease resistance (e.g., known fungal, bacterial, viral, insect, or nematode diseases); resistance to environmental extremes (e.g., drought, temperature, salinity); and horticultural characteristics (e.g., habit, flowering time etc.). The method may also be used to alter or modulate the effect of genes present in plants, e.g., by transformation with antisense constructs, or with "sense constructs" (see Napoli et al., 1990, The Plant Cell 2:279–289 and van der Krol et al., 1990, The Plant Cell 2:291–299).

The method may also be used as a means to generate somaclonal variation in chrysanthemums, as an alternative to known methods, e.g. treatment with radiation or chemical mutagens. While not being bound by any theory or mechanism, it is believed that interaction of introduced Agrobacterium DNA or pieces of the same with endogenous plant components, e.g., plant nucleases may lead to the creation of somaclonal variants. This may provide a milder and more controllable means of generation of somaclonal variation than existing methods. This approach provides a means to produce a variety of new, readily selectable traits in host chrysanthemums, unrelated to the particular DNA actually introduced by the Agrobacterium.

The following examples illustrate the practice of the present method.

6. EXAMPLE 1: TRANSFORMATION OF *DENDRANTHEMA GRANDIFLOR* VARIETY TOON HERMANS

6.1. GROWTH OF SOURCE PLANTS

Rooted, in vitro shoots of *Dendranthema grandiflora* variety Toon Hermans were obtained from Fides (Holland). They were maintained and propagated by putting nodal segments into Magenta G-7 (Magenta Corp.) boxes with 80 ml of an MS-based medium (MS major salts, minor salts and iron (Murashige et al., 1962, *Phys, planta.* 15:473–497), B-5 vitamins (Gamborg et al., 1968, *Exp Cell Res.* 50:148–151), 3% sucrose (Sigma), 3 mM 2-(N-Morpholino) ethanesulfonic acid, (MES) (Sigma), pH 5.7 (with KOH) which had been solidified with 0.7% Tissue Culture agar (Hazelton Biologics, Inc.) or 0.2% Gelrite (Scott Laboratories, Inc.) and autoclaved at 15 lbs/square inch, 250° C. for 20 minutes.

The in vitro plants were grown in a 24° C. controlled environment room under 12 hours illumination/day, 2–3000 lux (30–40 uE/m2s) of plant spectrum fluorescent illumination (Agro Lite, Philips). The first two to three nodes of the growing plant were excised and returned to new MAGENTA® boxes with the same medium approximately every six weeks.

6.2. PREPARATION OF AGROBACTERIUM INOCULUM

Figure 1:
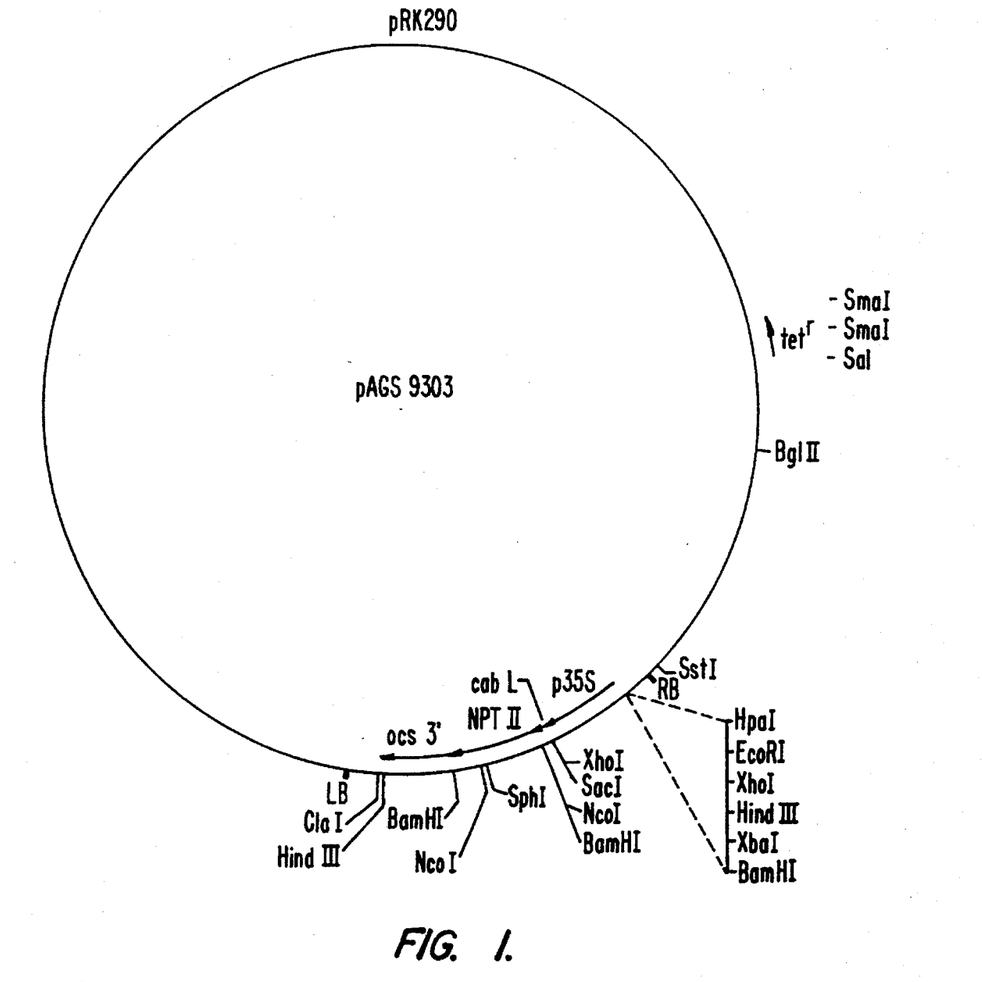
FIG. 1 is a schematic showing component parts and restriction sites of pAGS9303.

*Agrobacterium tumefaciens* strain LBA4404 (Hoekema et al., 1983 *Nature* 303:179–181) containing the binary vector pAGS9303 which contains the Cauliflower Mosaic Virus 35S promoter and neomycin phosphotransferase II (NPTII) gene which confers kanamycin resistance, (see FIG. 1 for a schematic illustration) were maintained on Minimal A (Davis et al., 1950, *J. Bacteriol.* 60: 17–28) plates (Minimal A–), 10.5 g/l $K_2HPO_4$ (Baker Chemical Co. ), 4.5 g/l $KH_2PO_4$ (Fischer Scientific Co.), 1.0 g/l $(NH_4)_2SO_4$ (Sigma), 0.5 g/l Na Citrate $2H_2O$ (Curtis Matheson Scientific), 1 mM $Mg_2SO_4.7H_2O$ (Sigma), 2 g/l glucose (Sigma), solidified with 15% Bactoagar (Difco) containing 1.0 mg/l tetracycline (Sigma). The disarmed strain LBA4404 alone was used as a control inoculum. The strain was maintained on Mina plates. For each of the Agrobacteria plates inoculated into 30 ml of liquid Mina in a 250 ml Erlenmeyer flask and agitated at 150 rpm at 28° C. for 4 hours. An inoculum of approximately $3 \times 10^7$ cells/ml was used.

6.3. PREPARATION OF EXPLANTS

Partially to fully expanded leaves and petioles from the in vitro plants were removed and placed in a few mls of sterile distilled water in a 150×20 mm petri plate. Two 4 mm wide sections of petiole and leaf were made.

6.4. INOCULATION AND INCUBATION OF EXPLANTS

The sterile water was removed by pipet and the inoculum was pipetted on in its place. The explants were then removed from the inoculum and placed on incubation medium plates, specifically, MS-based as in Section 6.1., supra, above with 0.2% Gelrite, 2.0 mg/l 6-BA (Sigma), 1.0 mg/l NAA (Sigma) 200 μM 3',5'-dimethoxy-4'-hydroxyacetophenone (acetosyringone) (Aldrich) on 7.0 cm sterile Whatman #1 filter paper circles. The incubation medium plates were incubated at room temperature (around 22° C.) for 3 days (approximately 72 hours).

6.5. PLACEMENT ON SELECTION MEDIUM

Following the incubation period, explants were transferred to selection medium plates, specifically, MS-based medium as in 6.1., supra, solidified with 0.2% Gelrite, with 2.0 mg/l 6-BA, 1.0 mg/l NAA, 500 mg/l Geopen (carbenicillin, Pfizer Roerig) and either 10, 25, 50 or 100 mg/l kanamycin sulfate (Sigma)). Plates were placed in clear plastic boxes and put in a 24° C. controlled environment room, 12 hours illumination/day, 1500–2500 lux, plant spectrum lights. After 1 month, the explants were transferred to plates of the same medium but without kanamycin sulfate, and were cultured for another 3 weeks as above. Regenerated shoots were then removed from the explants and placed on rooting medium, specifically, MS-based medium as in 6.1., supra, solidified with 0.2% Gelrite, with 500 mg/l Geopen (carbenicillin). If the regenerated shoots were mature and elongated, they were placed on rooting medium with 50 mg/l kanamycin sulfate to confirm transformation. These shoots were evaluated after 16 days for rooting in the presence of kanamycin sulfate. The remaining shoots were tested for rooting on 50 mg/l kanamycin after elongation and maturation for 2 weeks on rooting medium. These shoots were evaluated after 11 days and one month for rooting in the presence of kanamycin sulfate.

6.6. RESULTS

A total of 8 Toon Hermans transformants were produced. The transformation efficiencies (number of confirmed shoots divided by the number of explants×100) for different kanamycin levels are tabulated below in Table I.

TABLE I

| Kanamycin Level | Number of Explants | Number Confirmed Shoots | Transformation Efficiency |
|---|---|---|---|
| 10 | 46 | 0 | |
| 25 | 38 | 3 | 8.0% |
| 50 | 37 | 1 | 3.0% |
| 100 | 42 | 4 | 9.5% |

7. EXAMPLE 2: TRANSFORMATION OF *DENDRANTHEMA GRANDIFLORA* VARIETY WITH CYTOKININ PRETREATMENT OF IMPALA SOURCE PLANTS

7.1. GROWTH OF SOURCE PLANTS

Non-pretreated source plants were grown as in Section 6.1., supra, except the variety was Impala (Fides, Holland).

To obtain cytokinin-pretreated source plants, shoot tips (apex and 3–4 pairs of leaf primordia and leaves) of in vitro Impala plants were placed on proliferation medium, specifically, MS-based medium as in Section 6.1., supra, solidified with 0.2% Gelrite and with 2 mg/l kinetin (Sigma) and 0.02 mg/l NAA (Sigma). Multiple shoots proliferated from the original shoot tips on this medium. Single shoot tips were transferred monthly from the proliferation medium to new plates of the same medium. The plates containing the shoot cultures were maintained in a 24° C. controlled environment room, under 12 hours illumination/day 2–3000 lux plant spectrum illumination (Agro Lite, Philips).

7.2. PREPARATION OF AGROBACTERIUM INOCULUM

Figure 2:
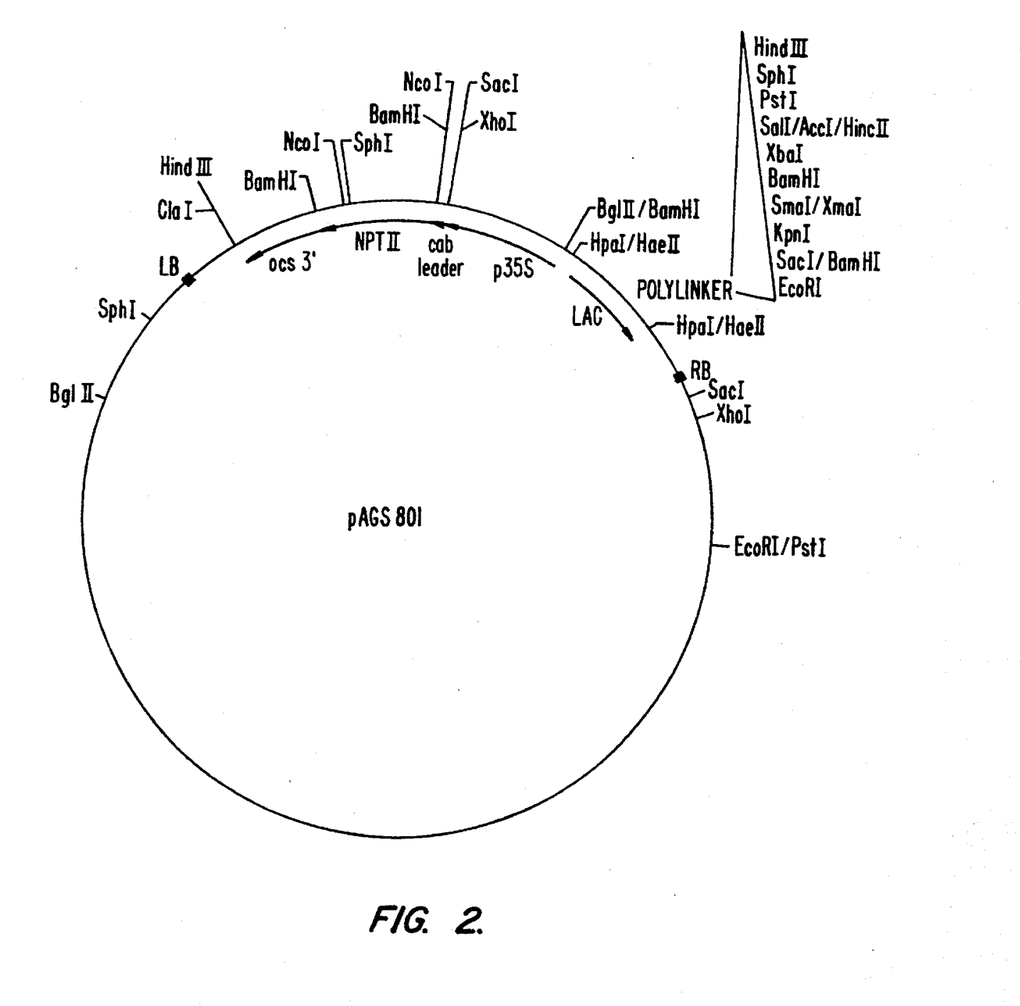
FIG. 2 is a schematic showing component parts and restriction sites of pAGS801.

The preparation of Agrobacterium inoculum was carried out as in Section 6.2., supra, with the following differences. The binary vector used was pAGS801 containing 35S-NPTII, (neomycin phosphotransferase II) and is shown in FIG. 2. The inoculum was agitated for 24 hours at 150 rpm at 28° C. and used without calculating cell concentration.

7.3. PREPARATION OF EXPLANTS

Preparation of explants both from pretreated and non-pretreated source plants was carried out as in Section 6.3., supra.

7.4. INOCULATION AND INCUBATION OF EXPLANTS

The explants were inoculated with Agrobacterium inoculum using the same procedure as described in Section 6.4., supra. The inoculated explants were incubated in incubation medium described in Section 6.4., supra, except that 2 phytohormone combinations were used in addition to 2 mg/l 6-BA, 1 mg/l NAA. In these formulations, either 1 mg/l 6-BA, 0.1 mg/l NAA or 0.5 mg/l 6-BA, 0.5 mg/l NAA were used instead of 2 mg/l 6-BA, 1 mg/l NAA. The incubation conditions were the same as those described in Section 6.4., supra.

7.5. PLACEMENT ON SELECTION MEDIUM

Following the incubation period, explants were transferred to selection medium plates as in Section 6.5., supra, with the following differences. The phytohormone formulations were as in the incubation medium above. The kanamycin sulfate selection levels were 10, 25, 50, and 100 mg/l. The explants were transferred to the same medium without kanamycin after one month. Three weeks later, shoots were removed from the explants and placed on rooting medium (as in Section 6.5., supra, except kanamycin sulfate at a concentration of 75 mg/l was used). Shoots were evaluated after 2 weeks for rooting on kanamycin-containing medium.

7.6. RESULTS

A total of 6 Impala transformants were produced. The transformation efficiencies (# of confirmed shoots divided by the number of explants×100) for different kanamycin levels for pretreated vs non-pretreated shoot cultures are tabulated below in Table II. Pretreated explants yielded transformants.

TABLE II

| Kanamycin Selection Level mg/l | Pretreated | | | Non-Pretreated | | |
|---|---|---|---|---|---|---|
| | A | B | C | A | B | C |
| 1. Hormone formulation - 2 mg/l 6-BA 1 mg/l NAA | | | | | | |
| 0   | 19 | 3 | 16%  | 8  | 0 | 0 |
| 25  | 24 | 0 | 0    | 14 | 0 | 0 |
| 50  | 28 | 0 | 0    | 21 | 0 | 0 |
| 100 | 21 | 0 | 0    | 21 | 0 | 0 |
| 2. Hormone formulation - 1 mg/l 6-BA 0.1 mg/l NAA | | | | | | |
| 0   | 29 | 0 | 0    | 21 | 0 | 0 |
| 25  | 18 | 0 | 0    | 14 | 0 | 0 |
| 50  | 15 | 0 | 0    | 19 | 0 | 0 |
| 100 | 30 | 1 | 0.3% | 18 | 0 | 0 |
| 3. Hormone formulation - 0.5 mg/l 6-BA 0.5 mg/l NAA | | | | | | |
| 0   | 27 | 0 | 0    | 17 | 0 | 0 |
| 25  | 17 | 1 | 6%   | 15 | 0 | 0 |
| 50  | 31 | 1 | 3%   | 15 | 0 | 0 |
| 100 | 38 | 0 | 0    | 17 | 0 | 0 |

A: Number of explants
B: Number of transformed shoots
C: Transformataion efficiency

8. EXAMPLE 3: *TRANSFORMATION OF DENDRANTHEMA GRANDIFLORA* VARIETY INDIANAPOLIS WHITE GIANT #4

8.1. GROWTH OF SOURCE PLANTS

Rooted cuttings of *Dendranthema grandiflora* variety Indianapolis White Giant #4 were obtained from Yoder Brothers (Salinas, Calif.). These were grown under long day conditions (approximately 16 hour light/day) for about 2½ months. The plants were then moved to a controlled environment chamber (Conviron, Controlled Environments, Winnepeg, Canada) and illuminated for 10 hr./day with approximately 7–10,000 lux of mixed, fluorescent/incandescent light, 22° C. day temperature, 18° C. night temperature, for 4 weeks.

8.2. PREPARATION OF AGROBACTERIUM INOCULUM

Figure 3:
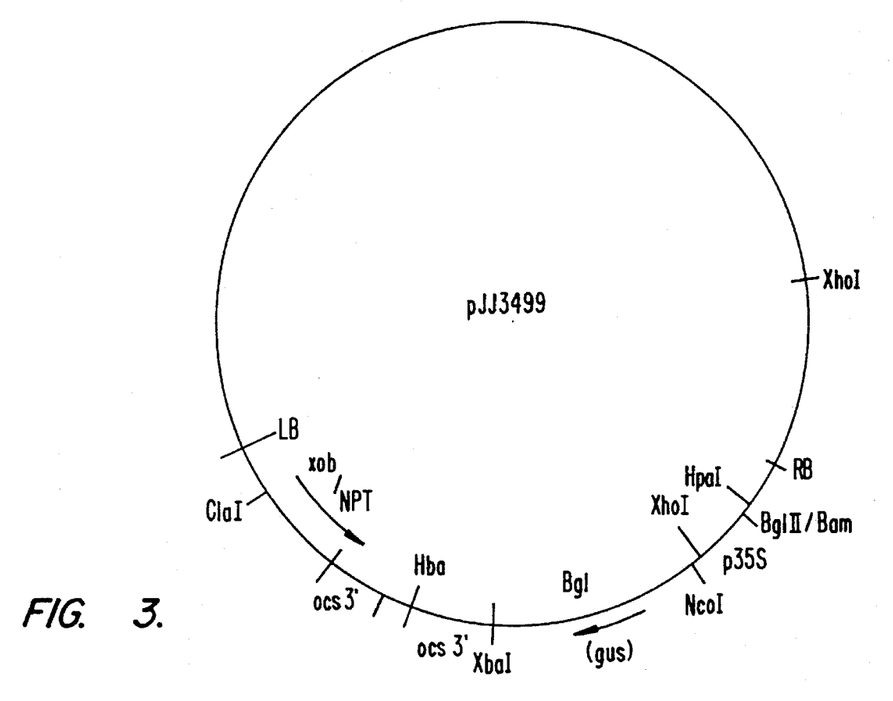
FIG. 3 is a schematic showing component parts and restriction sites of pJJ3499.

*Agrobacterium tumefaciens* strain LBA4404 (Hoekema, 1983, Nature 303:179–181) containing binary vector pJJ3499 was maintained as in Section 6.2., supra. The disarmed strain LBA4404 alone was used as a control inoculum and was maintained as in Section 6.2., supra. The binary vector pJJ3499 is described in FIG. 3. It contains a nos promoter promoting the expression of the NPTII gene and a 35S promoter promoting the expression of the β-glucuronidase gene within the T-DNA borders.

For each of the Agrobacteria, a loop of bacteria was inoculated into 6 ml of liquid MINA as described in Section 6.2., supra, and grown at 28° C. agitated at 150 rpm. The following day, the culture was diluted into 24 ml liquid Mina in a 250 ml Erlenmeyer flask and grown for 5 additional hours, at which time the OD550 was determined. The cultures were diluted to $8.7 \times 10^8$ cell/ml for use as inocula.

8.3. PREPARATION OF EXPLANTS

Flowering stalks, 4 weeks after initiation of short day (10 hr. illumination/day) conditions, were cut 10–15 cm down from the shoot apex and placed immediately in water. The stalks were then trimmed of leaves (except the apex) and rinsed 2–3 seconds in 70% ETOH water. They were then placed in 2 liters of 20% chlorine bleach containing 1.05% NaOHCl (All Pure Chemical Co.) and 0.1% Tween 80 (Sigma) solution which was stirred for 20 minutes. The flower stalks were rinsed in 2 liters of sterile water with stirring and transferred to a second rinse in sterile distilled water until used.

Bleached or injured tissues were removed aseptically with a scalpel, and the peduncles (flower stem) were cut into 3–5 mm cross sections from below the bud to 4 cm down the stem. The peduncle sections were collected in a sterile petri plate.

8.4. INOCULATION AND INCUBATION OF EXPLANTS

The inocula were pipetted onto the peduncle explants, and then excess liquid was removed by pipette. The explants were then placed on incubation medium plates, specifically, MS-based medium as described in Section 6.4., with 1.0 mg/l kinetin (Sigma); 0.1 mg/l IAA (Sigma), 0.1 mg/l gibberellic acid (GA) (Sigma) and 100 μM acetosyringone, solidified with 0.7% Tissue Culture Agar on 7.0 cm sterile Whatman #1 filter paper circles. One cut surface was in contact with the filter paper. The incubation medium plates were incubated at room temperature (about 22° C.) for 4 days (approximately 96 hrs.).

8.5. ANTIBIOTIC WASH AND PLACEMENT OF SELECTION MEDIUM

Following the incubation period, the explants were washed in an antibiotic solution, specifically, MS-based medium as in Section 6.1., supra, with 500 mg/l cefotoxine (Calbiochem)) by pipetting 25–30 mls of the solution onto the incubation plates and agitating the plates at 100 rpm for about 2 hrs.

The explants were then placed, with a cut surface in contact with the medium, on selection medium plates, specifically, MS-based medium, as in Section 6.1., supra, solidified with 0.7% Tissue Culture Agar, with 1.0 mg/l kinetin, 0.1 mg/l IAA, 0.1 mg/l GA, 100 mg/l vancomycin (Sigma) and 0 (explants inoculated with strain LBA4404) or 25 mg/l kanamycin sulfate (explants inoculated with strain LBA4404/PJ33499). Plates were wrapped with parafilm (American Can Company) and placed in a 24° C. controlled environment cabinet (Percival, Boone, Iowa) 16 hr. illumination/day, 2–4000 lux, cool white (Sylvania) fluorescent lights. One month later the calli which appeared on the explants were transferred to new plates of the same medium.

After another month, one shoot was transferred to rooting medium (as in Section 6.5., supra, except kanamycin sulfate at 25 mg/l and vancomycin at 300 mg/l instead of Geopen carbenicillin were used. The remaining dark green morphogenic calli were transferred to a shoot maturation medium, specifically MS-based medium as in Section 6.1., supra, solidified with 0.7% Tissue Culture Agar, except with 1 mg/l kinetin, 10% w/v coconut water (Gibco), 25 mg/l kanamycin sulfate. After one week, the majority of the calli were transferred to a second shoot maturation medium, specifically, MS-based medium as in Section 6.1., supra, solidified with 0.7% Tissue Culture Agar, except with 1 mg/l kinetin, 10 mg/l GA, 300 mg/l vancomycin and 25 mg/l kanamycin sulfate. After 6 weeks on this medium, shoots were transferred to rooting medium specifically, MS-based medium as in Section 6.1., supra, solidified with 0.7% Tissue Culture Agar, with 25 mg/l kanamycin sulfate and 300 mg/l vancomycin for elongation and rooting. Plants which rooted in the presence of 25 mg/l kanamycin sulfate were confirmed for transformation by a leaf callusing assay. Sections of leaf from regenerated shoots, 0.5 cm×0.5 cm, were placed on callusing medium, specifically, MS-based medium as in Section 6.5., supra, solidified with 0.7% Tissue Culture Agar, with 1.0 mg/l NAA, 0.1 mg/l 6-BA; 0.1 mg/l 2,4-D (Sigma), 25 mg/l kanamycin sulfate, 300 mg/l vancomycin. Leaf pieces were evaluated for callus production after 2–3 weeks.

A histochemical β-glucuronidase (GUS) assay (Jefferson, 1986, Proc. Natl. Acad. Sci. U.S.A. 83:8447–8451) was performed on two of the transformants, as well as on negative (chrysanthemum) and positive (tobacco) controls. Leaf discs were punched with a #1 cork borer from leaves of the transformants and the controls. The discs were placed in wells of a 96 well microtiter plate (Falcon) in 100 μl of 90 mM $K_2HPO_4$ pH 7 buffer with 2 μl/ml triton:ethanol:water, 1:4:5 and with 1.0 μg/ul 5-bromo-4-chloro-3-indolyl glucuronide (X-Gluc, Molecular Probes, Inc., Eugene, Oreg.). The tissue in the assay buffer was briefly vacuum infiltrated and incubated at room temperature overnight.

8.6. RESULTS

Seventy-one percent of explants produced transformed calli. Of these, 28% were of a dark green translucent morphogenic type with the potential to develop into shoots; 55% of those calli developed into transformed shoots. A total of 5 plants of Indianapolis White Giant #4 transformed with pJJ3499 were produced. The transformation efficiency (number of confirmed shoots divided by the number of explants×100) was 11% (5/45).

The GUS assay was positive for both transformants tested, as well as the positive control. It was negative for the negative control.

9. DEPOSIT OF MICROORANISMS

*Agrobacterium tumefaciens* strain LBA4404 which contains the plasmid pAGS801, has been deposited with the Agricultural Research Culture Collection (NRRL) Peoria, Ill. on Aug. 17, 1990 and assigned accession number NRRL B-18708.

The invention described and claimed herein is not to be limited in scope by the specific embodiments herein disclosed, since these embodiments are intended as illustrations of several aspects of the invention. Any equivalent embodiments are intended to be within the scope of this invention. Indeed various modifications of the invention in addition to those shown and described herein will become apparent to those skilled in the art from the foregoing description. Such modifications are also intended to fall within the scope of the appended claims.

Various references are cited herein, the disclosures of which are incorporated by reference in their entireties.

What is claimed is:

1. A method for producing a chrysanthemum plant comprising an exogenous DNA fragment, which chrysanthemum plant is capable of expressing a gene within the exogenous DNA fragment, comprising the steps of:

(a) isolating an explant from source material from a chrysanthemum plant, wherein said source material is selected from the group consisting of leaf, stem, peduncle, petiole, meristem, and shoot apex;

(b) inoculating the explant from source material from the chrysanthemum plant with a culture of Agrobacterium, which Agrobacterium comprises an exogenous DNA fragment comprising a gene under the control of a promoter capable of promoting the transcription of the gene within the exogenous fragment, to obtain an inoculated explant;

(c) incubating the inoculated explant of step (b) on an incubation medium;

(d) culturing the incubated explant of step (c) on a regeneration medium to obtain regenerated shoots of the chrysanthemum plant; and (e) culturing the regenerated shoots of step (d) on a rooting medium to obtain a chrysanthemum plant comprising the exogenous DNA fragment, in which the chrysanthemum plant is capable of expressing the gene within the exogenous DNA fragment.

2. The method according to claim 1 in which the explant is selected from the group consisting of a leaf, a petiole, a stem, and a peduncle.

3. The method according to claim 1 in which the explant is a leaf explant.

4. The method according to claim 1 in which the transcriptional promoter is selected from the group consisting of the 35S promoter, the 1' promoter, the 2' promoter and the nopaline synthetase promoter.

5. The method of claim 1 which further comprises sterilizing the explant before contacting the explant with the culture of Agrobacterium.

6. The method according to claim 1 in which the exogenous DNA fragment comprises a gene encoding a selectable marker.

7. The method according to claim 6 in which the selectable marker is kanamycin resistance.

8. The method according to claim 6 in which the selectable marker is hygromycin resistance.

9. The method according to claim 6 in which the selectable marker is spectinomycin resistance.

10. The method according to claim 1 in which the exogenous DNA fragment comprises a gene encoding a reporter substance.

11. The method according to claim 10 in which the reporter substance is β-glucuronidase.

12. The method according to claim 10 in which the reporter substance is luciferase.

13. The method according to claim 1 in which the incubation medium comprises amounts of a nutrient medium, an energy source comprising a sugar, soluble ferrous or ferric iron, and a cytokinin effective to facilitate transformation of the inoculated explant.

14. The method according to claim 13 in which the cytokinin is selected from the group consisting of 6-BA, zeatin, kinetin, and 2-iP.

15. The method according to claim 14 in which the cytokinin is present in the amount of about 0.1–10 mg/l.

16. The method according to claim 14 in which the cytokinin is thidiazuron.

17. The method according to claim 16 in which the cytokinin is present in the amount of about $10^{-4}$–$10^{-2}$ mg/l.

18. The method according to claim 14 in which the incubation medium further comprises an auxin.

19. The method according to claim 18 in which the auxin is present at a concentration up to about 2.0 mg/l.

20. The method according to claim 18 in which the auxin is selected from the group consisting of IAA, NAA, 2,4-D, and picloram.

21. The method according to claim 18 in which the auxin is NAA.

22. The method according to claim 14 in which the incubation medium further comprises acetosyringone.

23. The method according to claim 22 in which the acetosyringone is present at a concentration up to about 500 µM.

24. The method according to claim 22 in which the acetosyringone is present as a concentration of about 200 µM.

25. The method according to claim 1 in which the inoculated explant of step (a) is incubated on incubation medium for about 1–5 days at a temperature of about 16°–28° C.

26. The method according to claim 1 which further comprises the step of washing the inoculated explant of step (b) with a solution comprising effective amounts of an antibiotic which is effective against Agrobacterium and which is nontoxic to the chrysanthemum plant before culturing the inoculated explant on the regeneration medium of step (c).

27. The method according to claim 26 in which the antibiotic is selected from the group consisting of carbenicillin, cefotaxime, and vancomycin.

28. The method according to claim 1 in which the regeneration medium comprises amounts of a nutrient medium, an energy source comprising a sugar, a soluble ferrous or ferric iron, a cytokinin, and a counter selection agent effective to induce shoot regeneration on the incubated explant.

29. The method according to claim 28 in which the regeneration medium further comprises an auxin.

30. The method according to claim 28 in which the counterselection agent is selected from the group consisting of carbenicillin, cefotaxime, and vancomycin.

31. The method according to claim 26 in which the regeneration medium further comprises a selection agent.

32. The method according to claim 31 in which the selection agent is kanamycin.

33. The method according to claim 31 in which the selection agent is hygromycin.

34. The method according to claim 31 in which the selection agent is spectinomycin.

35. The method according to claim 10 in which the reporter substance is an enzyme and in which the regeneration medium further comprises a reporter agent which is a substrate for the enzyme.

36. The method according to claim 11 in which the reporter agent is glucuronic acid.

37. The method according to claim 30 in which the incubated explant of step (c) is incubated in regeneration medium for about 10–60 days.

38. The method according to claim 1 in which the rooting medium comprises amounts of a nutrient medium, an energy source comprising a sugar, soluble ferrous or ferric iron, and a counter selection agent effective to induce root formation on the regenerated shoots to produce rooted plantlets.

39. The method according to claim 38 in which the rooting medium further comprises a selection agent.

40. The method according to claim 1 in which the regenerated shoot of step (d) is incubated in rooting medium for about 1–4 weeks.

41. The method according to claim 1 which further comprises the step of detecting conversion of a reporter agent in the regeneration medium to a detectable product in the presence of a reporter substance expressed by the incubated explant.

42. The method according to claim 1 which further comprises detecting the presence of the exogenous DNA fragment in the chrysanthemum plant by DNA detection means.

43. The method according to claim 12 in which the reporter agent is luciferin, respectively.

44. The method of claim 1 which further comprises growing the explant source material on a solid pretreatment medium comprising a nutrient medium, an energy source comprising a sugar, soluble ferrous or ferric iron, and a cytokinin before isolating the explant.

45. The method of claim 44 in which the explant source is a shoot tip.

46. The method according to claim 44 in which the nutrient medium is selected from the group consisting of White's, B5, LS, N6, and MS medium.

47. The method according to claim 44 in which the energy source is a sugar.

48. The method according to claim 44 in which the sugar is present in the amount of about 0.5–5%.

49. The method according to claim 44 in which the sugar is sucrose.

50. The method according to claim 44 in which the iron is present at a concentration of about 25–200 µM.

51. The method according to claim 44 in which the cytokinin is selected from the group consisting of 6-BA, zeatin, kinetin, and 2-iP.

52. The method according to claim 51 in which the cytokinin is present in the amount of about 0.1–10 mg/l.

53. The method according to claim 44 in which the cytokinin is thidiazuron.

54. The method according to claim 53 in which the cytokinin is present in the amount of about $10^{-4}$ mg/ml to $10^{-2}$ mg/ml.

55. The method according to claim 44 in which the pretreatment medium further comprises an auxin.

56. The method according to claim 55 in which the auxin is present in the amount up to about 0.5 mg/l.

57. The method according to claim 55 in which the auxin is selected from the group consisting of IAA, NAA, 2,4-D, and picloram.

58. The method according to claim 55 in which the auxin is NAA.

59. The method according to claim 44 in which the explant source is incubated in a pretreatment medium for about one day to about seven months.

60. A method for producing a chrysanthemum plant comprising an exogenous DNA fragment using Agrobacterium as a vector, comprising the steps of:

(a) incubating chrysanthemum plant source material on a pretreatment medium;

(b) isolating a leaf explant from source material from the chrysanthemum plant;

(c) inoculating the explant from source material from the chrysanthemum plant with a culture of Agrobacterium, which Agrobacterium comprises an exogenous DNA fragment comprising a gene under the control of a promoter capable of promoting the transcription of the gene within the exogenous fragment, to obtain an inoculated explant;

(d) incubating the inoculated explant of step (c) on an incubation medium;

(e) culturing the incubated mixture of step (d) on a regeneration medium to obtain regenerated shoots of the chrysanthemum plant; and (f) culturing the regenerated shoots of step (e) on a rooting medium to obtain a chrysanthemum plant comprising the exogenous DNA fragment.

61. The method of claim 60 which further comprises sterilizing the explant before contacting the explant with a culture of Agrobacterium comprising the exogenous DNA fragment.

* * * * *